United States Patent [19]
Truppe

[11] Patent Number: 5,842,858
[45] Date of Patent: Dec. 1, 1998

[54] METHOD OF IMAGING A PERSON'S JAW AND A MODEL THEREFOR

[75] Inventor: Michael Truppe, Vienna, Austria

[73] Assignee: Artma Biomedical, Inc., Salt Lake City, Utah

[21] Appl. No.: 645,280

[22] Filed: May 13, 1996

[30] Foreign Application Priority Data

May 11, 1995 [EP] European Pat. Off. ............. 95 89 0092

[51] Int. Cl.$^6$ .................................................. A61C 19/04
[52] U.S. Cl. ............................................ 433/69; 433/215
[58] Field of Search ............................ 433/69, 213, 214, 433/215; 128/777

[56] References Cited

U.S. PATENT DOCUMENTS

| | | | |
|---|---|---|---|
| 4,303,077 | 12/1981 | Lewin et al. | 433/69 |
| 4,836,778 | 6/1989 | Baumrind et al. | 433/69 |
| 4,859,181 | 8/1989 | Neumeyer | 433/69 |
| 5,015,183 | 5/1991 | Fenick | 433/76 |
| 5,340,309 | 8/1994 | Robertson | 433/215 |

Primary Examiner—John J. Wilson
Attorney, Agent, or Firm—Herbert L. Lerner; Laurence A. Greenberg; Werner H. Stemer

[57] ABSTRACT

The jaw of a person and a model thereof is represented with a series of steps. A device for positional determination, which has marking points, is inserted into the oral cavity of the person, at least one picture of the jaw of the person is taken with an imaging process, such as X-ray, CT, MRI or the like, including the marking points in the picture. The picture is stored as a data set and the marking points are identified. After an impression is taken of the jaw, a model is created. The representation itself includes the following steps: a further 3D sensor is brought to the model of the jaw. Next, the device for positional determination is reinserted into the model of the jaw in the same position as when the picture was taken. The positional relationship is determined between a 3D sensor on the device and the 3D sensor on the model of the jaw. After the device has been removed, a further 3D sensor is brought to the model of the jaw and inserted in the same position as when the picture was taken. Then the positional relationship is determined between the 3D sensor of the device and the 3D sensor on the model of the jaw. An optical image and the data set are superimposed in the positionally correct relationship, or alternatively, an optical image of the model of the jaw and the data set as superimposed in positionally correct association.

28 Claims, 2 Drawing Sheets

METHOD OF IMAGING A PERSON'S JAW AND A MODEL THEREFOR

BACKGROUND OF THE INVENTION

1. Field of the Invention

The invention relates to a method for representing the jaw of a person and/or a model of it.

2. Description of the Related Art

When dental implants are prepared, precise planning of the surgical operation is necessary. Various provisions for doing so are available. As a rule, an impression of the applicable jaw of the patient is taken, from which in turn a model of the jaw can be made. On the other hand, various imaging processes are suitable for giving the attending physician conclusive information about the particular situation. This may involve conventional X-ray images, CT scans, or MRI (Magnetic Resonance Imaging). It remains unsatisfactory, however, that the model on the one hand and the representation from the imaging process on the other cannot be made to match until this is done by the observer. Even more difficult is the task of having to make the actual situation during the operation itself match the model or the previously prepared representation.

European Patent Application EP-A 488 987 of the present Applicant discloses a method for representing moving bodies, in which an optical representation of the body and a data field associated with the body are simultaneously or alternatively represented from the same perspective and on the same scale in real time. Such a method is suitable in principle for solving the problems discussed above. An optical image of the applicable jaw is displayed on a monitor, and at the same time the associated data set, or in other words the result of the imaging process, is displayed. A position sensor should be brought to the applicable body parts, which sensor assures that the data set will shift in accordance with any incident motion of the body part, such as the lower jaw in the present instance. However, a prerequisite of this method is an initial setting of the system in which characteristic points of the data set are identified and are made to match the corresponding characteristic points in the visual representation. Precisely when such a method is employed for the human jaw, however, major problems arise, since the requisite characteristic points are not available in adequate numbers. This is especially true for a toothless jaw. Moreover, the required accuracy in the region of the jaw makes such an adjustment problematic even when teeth are present.

So-called articulators are also known for determining the position of the lower jaw. With them, the location of the virtual longitudinal axis of the lower jaw, for instance, can be determined. However, such articulators are not suitable for solving the above-described problem, since the oral cavity must be freely accessible in the operation itself.

Another option, of applying marking points to the skin on the outside of the jaw, is not feasible, since the patients are normally anesthetized during the operation. For that purpose they are intubated through the nose, causing complete relaxation of the facial musculature, which makes the marking points shift. This makes it impossible to use these points for position determination. Securing a marking body through the skin even when the picture is taken is generally impossible because of the burden it puts on the patient.

A method is also known from U.S. Pat. No. 5,383,454 in which a device for position determination is mounted on the outside of a patient's head. Although this device is very helpful, it is nevertheless difficult to detect the lower jaw precisely with it. Nor is it readily possible to use a relatively old picture, because it would then be very difficult to secure the device again in the same position.

SUMMARY OF THE INVENTION

One object of the invention is to overcome these disadvantages and to create a method that enables careful planning of a surgical operation in the region of the jaw from a model and in which representations from imaging methods can be incorporated in a vivid way. Another object of the invention is to enable monitoring of the particular status attained during a surgical operation itself, by making available an optical representation of the operative region that is positionally correctly superimposed with the result of the imaging process.

According to the invention, in a first aspect of the invention, this is attained by performing the following steps:

1. Preparatory steps: they can be done at any time before the actual representation; all that must be demanded is that the jaw not change, for instance from treatment by a dentist, between when these steps are performed and the representation.

Inserting a device for positional determination, which has marking points, into the oral cavity of the person; an essential feature of the device is that it occupies an unequivocally and precisely reproducible position in the oral cavity. The marking points should yield good contrast in whatever imaging process is used and should thus be easily identifiable. In the case of X-ray images, these may be lead beads, for instance, that are firmly embedded in plastic material. The corners of a wire structure or the like, built into the device, may also serve as marking points. The position sensor itself described hereinafter is at this point not necessarily present in or attached to the device. It is, however, essential that this position sensor subsequently be connectable to the device in a positionally unambiguous way.

Taking at least one picture of the jaw of the person with an imaging process, such as X-ray, computed tomography (CT), MRI or the like, including the marking points in the picture, and storing the picture in memory as a data set; this so-called digitization is a prerequisite for later processing of the picture.

Identification of the marking points; this can be done by hand, for instance by searching with the cursor on a screen for one marking point after another and thus identifying it. This means that the coordinates of the marking points are fixed in the coordinate system of the picture. It is entirely possible as well, however, to use a pattern recognition method for identification purposes.

2. Steps for performing the actual representation: these steps are performed on the occasion of an examination of the person or during an operation.

Bringing a 3D sensor to the outside of the applicable jaw; this is effected for instance by screwing the mount for the 3D sensor through the skin in the region of person's chin, if it is the lower jaw that is to be represented. Naturally it is also possible to prepare both the lower jaw and the upper jaw for the representation by using two sensors.

Reinserting the device for positional determination, if it has been removed in the meantime, into the oral cavity in the same position as when the picture was taken, the device being equipped with a 3D sensor. It is possible in principle for the picture to be made immediately before the representation. In that case, the device for position determination may still be in the mouth. In general, however, the device is reinserted in this step, and care should be taken that exactly the same location relative to the jaw be assumed as when the picture was taken. The 3D sensor must now be mounted on the device or built into it. It is essential that the location of this sensor be unambiguous with reference to the markings and be precisely known.

Determining the positional relationship between the 3D sensor of the device and the 3D sensor on the outside of the jaw; this is done by determining the three-dimensional location of the two sensors simultaneously, or nearly simultaneously.

Removing the device for positional determination; this establishes free access to the oral cavity.

Generating a superposition of an optical image of the jaw and the data set in the positionally correct relationship. Because of the sensor on the outside of the jaw, the current position of the jaw is always known. By carrying out a number of coordinate transformations, it is possible to position the data set such that the structures of the data set always still match, i.e., remain in agreement with, the corresponding structures of the optical image, even if the jaw should move three-dimensionally. If both jaws are provided with sensors, then one can switch back and forth between the lower jaw and the upper jaw in terms of the positionally correct representation. However, it is also possible to subdivide the data set into one part that applied to the lower jaw and one part that applies to the upper jaw; it is then possible to represent both the lower jaw and the upper jaw so that it is superimposed positionally correctly with the appropriate data set.

An essential feature of the present invention is that the step of initial adjustment of the relationship between the data set and the optical representation is substantially simplified. Once this association has been established in the first place, the method can proceed as described in EP-A 488 987. Since the position or location of the marking points in the device for position determination is known, it is unnecessary to scan these points with a 3D stylus, or to take other measures to adjust the system. The procedure can essentially be as described in U.S. Pat. No. 5,383,454.

In a second aspect of the present invention, the representation is not done with the applicable jaw itself; instead, a stereolithographic model of the jaw is made in a known manner. The positional determination device then fits into this model as well in an unambiguously determined position. In this way, the model can be represented with a positionally correctly superimposed data set. It is thus possible very comfortably and conveniently to carry out operation planning or to simulate various variants of an operation.

These two first aspects can be combined with one another, as a result of which the relationship of the actual jaw to the model can be represented very vividly. The optical representation can also be recorded, by making photographs or video recordings.

The representation itself can be done in the way described in EP-A 488 987. In it, a video camera provided with a position sensor is used to create an optical representation of the object, that is, of the jaw or the model, which is displayed on a suitable monitor. Since both the three-dimensional location of the camera and that of the object is known, a representation of the data set that corresponds to the same angle of view and the same scale can be calculated. The corresponding structures of the optical representation and from the picture of the imaging process thus coincide and can be represented in their correct position simultaneously or alternatively.

In an advantageous variant embodiment of the invention, however, it is possible that the generation of a superposition of the optical image and the data set be done such that a display of the data set is interpolated between the eye of the observer and the jaw or model of the jaw to be represented. Such a display can for instance be in the form of a transparent LCD (liquid crystal) display. The user then observes the real situation through the display on which the data set is represented at the same time. The superposition then takes place in the eye of the user. In general, both the user and the display are freely movable, although the peripheral condition must be met that the user can observe the object through the display. In that case, the user wears a 3D sensor and the display carries a 3D sensor as well, so that the appropriate perspective can again be calculated. Such a method for general objects has been described in Austrian Patent AT 398 163 of the present Applicant. This variant has the advantage that the user need not—except for the very small, light-weight sensor—wear any apparatus around his head. It is also possible in a simple way to give additional persons access to the representation.

It is furthermore possible in the same way within the scope of the invention, however, to embody the display as a pair of glasses or in some other way to connect it firmly to the head of the user. The use of semitransparent mirrors or other methods for reflecting into the eye of the observer are also possible in principle.

In an especially preferred variant of the method of the invention it is provided that three-dimensional structures are inserted by the user into the data set of the picture, and that the picture is represented in the positionally correct association with the optical image. In this way, not only can certain merely vague structures be emphasized in the picture, but a simulation can also be performed very simply. This is advantageous a change is to be made intentionally, for instance if in an orthodontic operation. The desired or planned final state can be drawn in. Situations can also be represented that result after the removal or addition of wedges of bone. Very accurate information about the feasibility and problems of such an operation can be obtained from the representation on the model.

The optical representation can also be done not merely "live" but also recorded, by taking photographs or making video recordings. If the position determining device also has optically visible marking points, then the method according to the invention can be modified slightly. The preparatory steps are the same as those in the above-described method. Hereinafter, for the sake of simplicity, the taking of photographs will be assumed. The same applies accordingly to video recordings. Depending on whether the pictures are to be taken of the jaw itself or of a model, such a model either will or will not be made. It is essential that at least one picture but even better two or more pictures each be taken from a same perspective, once with the position determining device in place and once without it. Since the marking points of the device are also visible on the photographs, they can be made to coincide with the X-ray image or the like on a monitor. It is possible in this way to determine the appropriate coordinate transformation. Since the photographs have been made from the perspective without the device, it is now possible to incorporate into them the data set from the imaging method, in a positionally correct way. This is essential, since it is first from this picture that the structures of interest are visible without hindrance by the device. In the event that a certain motion of the jaw has occurred between the taking of the different photographs, as is unavoidable in some cases, then the method is not impaired thereby since the position sensor mounted on the outside detects this motion, and a suitable correction is thus possible. In addition to the representation of the photographs, in this variant of the method the "live" representation, as described above, is naturally possible in addition. The method is simplified, since the position determining device need not have its own 3D sensor.

The present invention also relates to a device for positional determination which can be used for one of the above methods, wherein the device can be inserted into the oral cavity of a person and is embodied such that it can be held by the upper jaw and lower jaw of the person in an unambiguously reproducible position. This device is characterized in that it has marking points which are identifiable by an imaging method, and that it also has a position sensor which enables a precise determination of the three-dimensional position of the device. As has already described above, the position sensor may be omitted, as long as it is assured that with the built-in sensor the three-dimensional relationship between the sensor and the marking points is unambiguous and reproducible.

It is preferably provided that the device comprises a solid base body, which has the marking points and the position sensor, and that on this base body, retention bodies of a flexible, hardenable material are formed, which conform to the shape of teeth or the jaw. The device is first adapted to the jaw in the manner of an impression and after hardening can be used reproducibly in the same position.

BRIEF DESCRIPTION OF THE DRAWING

In a variant of the device, the device has marking points which are not only identifiable by an imaging method but are also optically visible.

The invention will be described in further detail below in terms of the exemplary embodiments shown in the drawing. Schematically shown in the drawings are:

DESCRIPTION OF THE PREFERRED EMBODIMENTS

Figure 2:
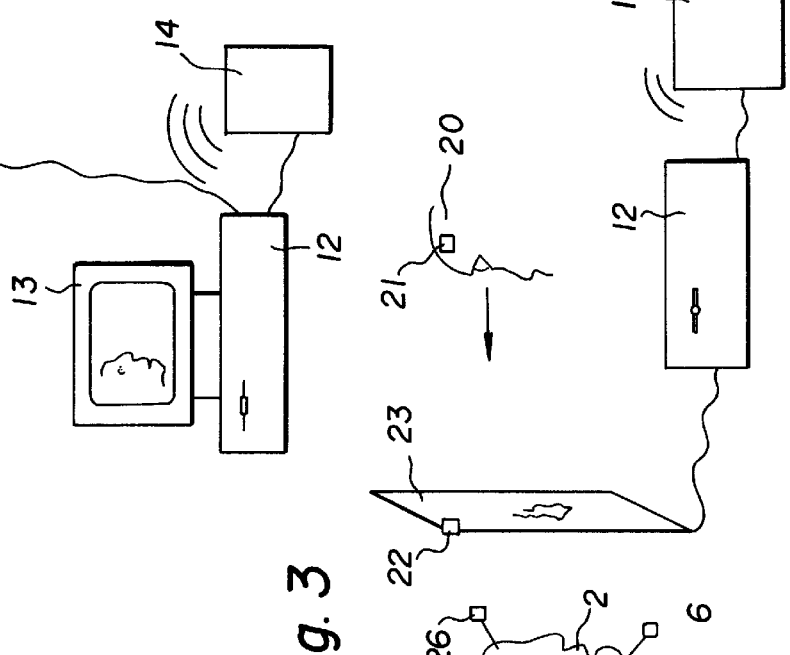
Figure 3:
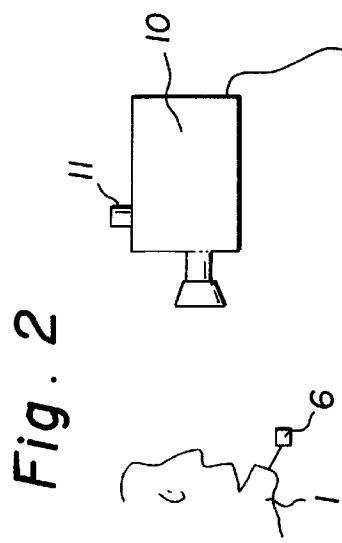
Figure 1:
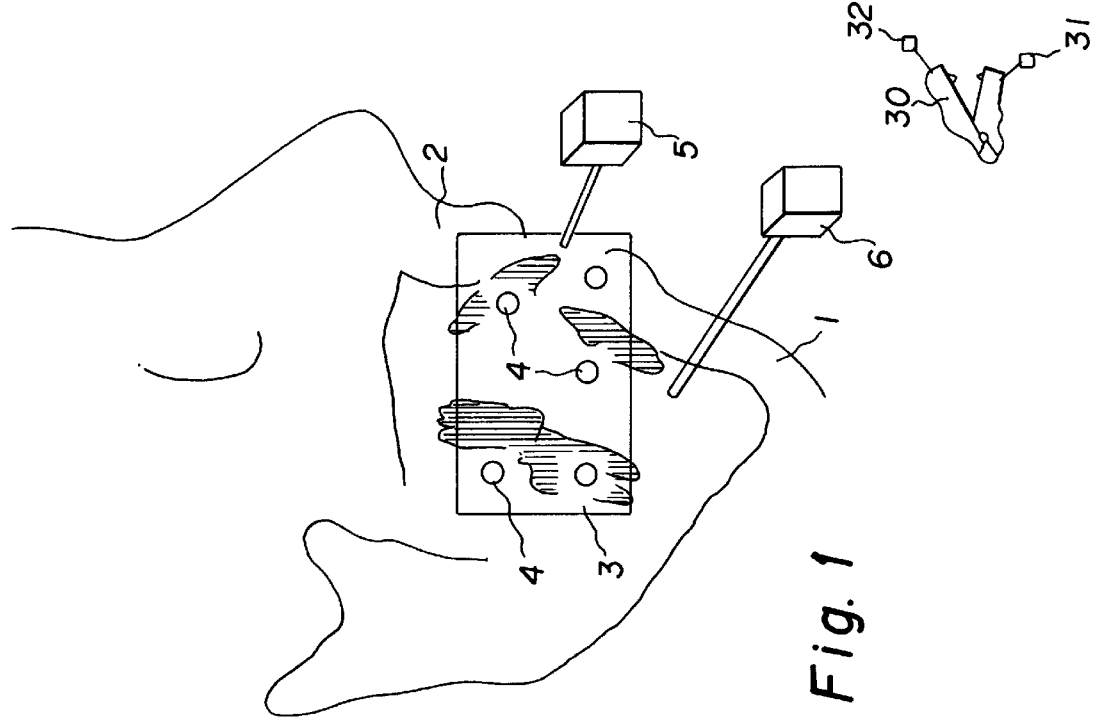
Figure 4:
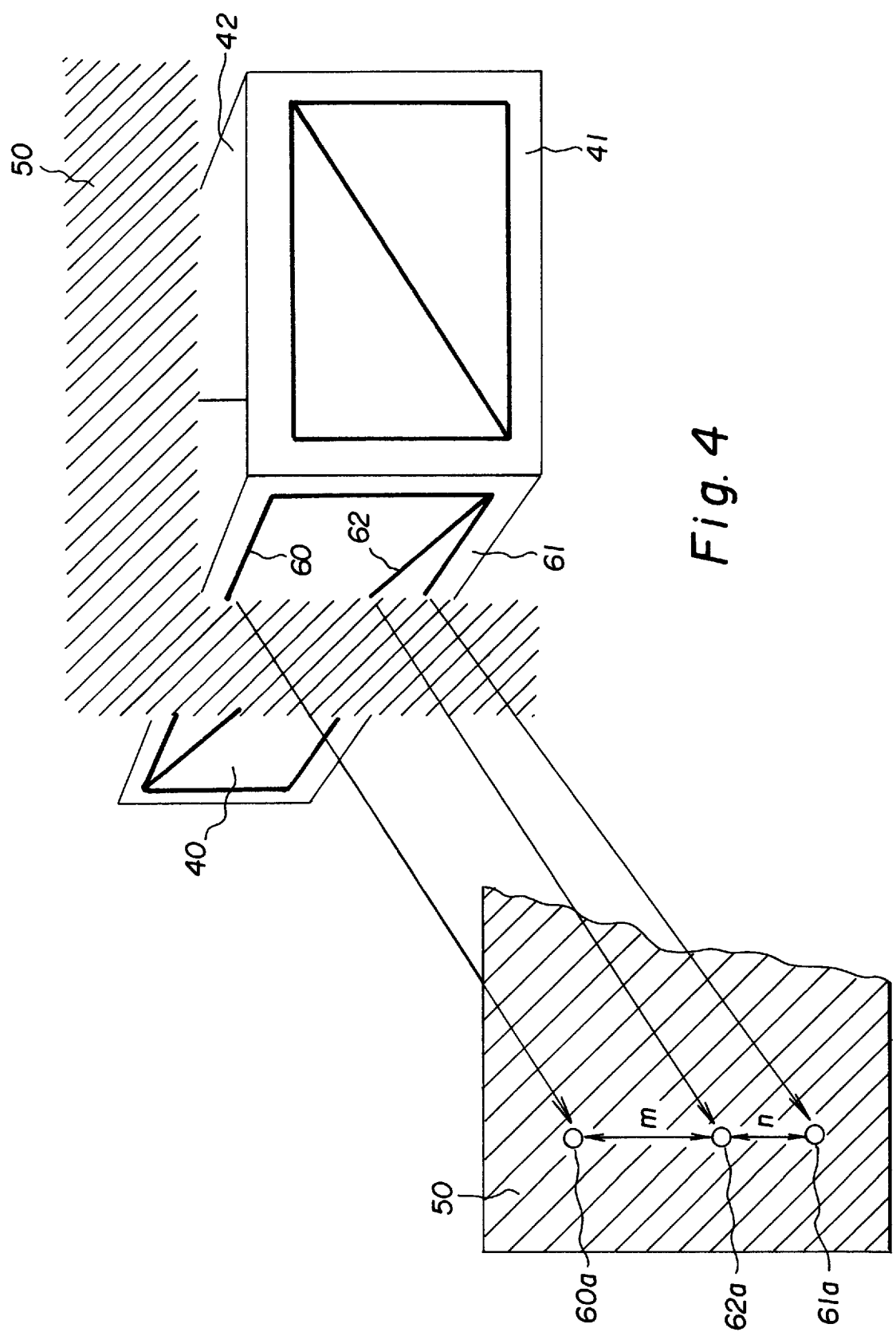

FIG. 1, a person with a position determining device, inserted into his oral cavity;

FIG. 2, a first system with which the method of the invention can be performed;

FIG. 3, a second system with which the method of the invention can be performed; and FIG. 4, a variant embodiment of marking points.

In FIG. 1, the head of a person is suggested with his lower jaw 1 and upper jaw 2. Located between them is a position determining device 3, which is embodied as a so-called splint that can be inserted in an unambiguously reproducible position. A number of marking points 4 are provided in this device 3 and can be seen clearly, for instance on an X-ray view. A 3D sensor 5 is firmly connected to the device 3. A further 3D sensor 6 is screwed to the outside of the lower jaw 1.

The system of FIG. 2 comprises a camera 10, on which a 3D sensor 11 is firmly mounted. The camera is connected via a computer 12 to a monitor 13 on which the lower jaw 1 can be represented. A picture taken by the imaging process is also stored in memory in the computer 12. The computer is also connected to a magnetic field emitter 14, which is disposed stationary in space. As a result, the three-dimensional location or position at any time can be detected, including the angular position of the sensors 6 and 11. The computer calculates a representation of the data set from the imaging process in real time and displays it on the screen.

In the variant embodiment of FIG. 3, the computer 12 is connected to a transparent LCD display 23, which has a 3D sensor 22. The user 20 also wears a 3D sensor 21. In addition to the sensor 6, which as in the previous variant embodiment is connected to the lower jaw 1, a sensor 26 is also provided here, mounted on the forehead and thus solidly connected to the upper jaw 2. The computer calculates a representation of the imaging process that corresponds to the position at the time of the jaw 1, 2, display 23, and observer 20 relative to one another. In the same way, a model 30 of the jaw, which is equipped with sensors 31, 32, can be observed.

FIG. 4 schematically shows an alternative for embodying the marking points, which are provided in or on the position determining device. Structures that produce contrast on the X-ray image or the like are disposed in three planes 40, 41, 42 at right angles to one another. Two of these planes 40, 42 are essentially parallel to the plane of symmetry of the head whenever the device 3 has been inserted into the jaw 1, 2. Each of the structures comprises a rectangle and a diagonal. Reference numeral 50 indicates an imaginary tomographic plane of a CT scan that is at right angles to the planes 40 and 42. In the corresponding representation of this CT layer 50, the upper side 60 of the rectangle appears as a dot or point 60a, the lower side 61 as a point 61a, and the diagonal 62 as a point 62a located between these points 60a and 61a. From the ratio of the distances m and n between the point 62a and the points 60a and 61a, respectively, the precise location of the layer 50 can be determined. It is possible in this way to correct the information in the CT relating to the feed motion of the table; this must be done if the patient has moved during the scanning operation, for instance.

The planes 40, 41, 42 with the above-described structures may either be integrated with the position determining device or connected to it by a rigid connection in such a way that they are located outside the jaws 1, 2.

I claim:

1. A method of representing a person's jaw, which comprises:

the preparatory steps of:
    inserting a device for positional determination, which has marking points, into a person's oral cavity;
    taking at least one image of the person's jaw, and including in the image the marking points, and storing the image in memory as a data set;
    identifying the marking points;

and the representing steps of:
    placing a first 3D sensor on the outside of the person's jaw;
    determining a positional relationship between the first 3D sensor and a second 3D sensor disposed on the device;
    removing the device for positional determination from the oral cavity; and
    generating a superposition of an optical image of the jaw and the data set in the positionally correct relationship.

2. The method according to claim 1, wherein the taking step comprises taking an image with an imaging process selected from the group consisting of X-ray, CT, and MRI.

3. The method according to claim 1, wherein the step of generating a superposition of the optical image and the data set comprises interpolating a display of the data set between an eye of an observer and the jaw of the jaw to be represented.

4. The method according to claim 3, wherein the interpolating step comprises displaying with a transparent LCD display.

5. The method according to claim 3, which comprises reflecting the data set into the observer's eye.

6. The method according to claim 1, which further comprises inserting three-dimensional structures into the data set of the image, and representing the image in the positionally correct relationship with the optical image.

7. The method according to claim 1, which further comprises removing the device following the taking step, and reinserting the device for positional determination into the oral cavity in a same position as in the taking step.

8. A method for representing a model of a person's jaw, which comprises:
   the preparatory steps of:
      inserting a device for positional determination, which has marking points, into a person's oral cavity;
      taking at least one image of the person's jaw, including the marking points in the picture, and storing the picture in memory as a data set;
      identifying the marking points;
      taking an impression of the jaw and forming a model of the jaw;
   and the representing steps of:
      inserting the device for positional determination into the model in a same position as in the taking step, the device being equipped with a 3D sensor;
      determining a positional relationship between the 3D sensor of the device and a second 3D sensor on the model of the jaw;
      removing the device for positional determination;
      generating a superposition of an optical image of the model and the data set in a positionally correct relationship.

9. The method according to claim 8, wherein the taking step comprises taking an image with an imaging process selected from the group consisting of X-ray, CT, and MRI.

10. The method according to claim 8, wherein the step of generating a superposition of the optical image and the data set comprises interpolating a display of the data set between an eye of an observer and a model of the jaw to be represented.

11. The method according to claim 10, wherein the interpolating step comprises displaying with a transparent LCD display.

12. The method according to claim 10, which comprises reflecting the data set into the observer's eye.

13. The method according to claim 8, which further comprises inserting three-dimensional structures into the data set of the image, and representing the image in the positionally correct relationship with the optical image.

14. A method for representing a person's jaw and a model thereof, which comprises:
   the preparatory steps of:
      inserting a device for positional determination, which has marking points, into a person's oral cavity;
      taking at least one image of the person's jaw, including the marking points in the picture, and storing the picture in memory as a data set;
      identifying the marking points;
      taking an impression of the jaw and forming a model of the jaw;
   and the representing steps of:
      bringing a first 3D sensor to the person's jaw;
      determining a positional relationship between the first 3D sensor and a second 3D sensor disposed on the device;
      removing the device for positional determination;
      bringing a further 3D sensor to a model of the jaw;
      inserting the device for positional determination into the model in a same position as in the taking step;
      determining a positional relationship between the 3D sensor of the device and a second 3D sensor on the model of the jaw;
      removing the device for positional determination;
      generating a superposition of an optical image of the jaw and the data set in a positionally correct relationship.

15. The method according to claim 14, wherein the taking step comprises taking an image with an imaging process selected from the group consisting of X-ray, CT, and MRI.

16. The method according to claim 14, wherein the step of generating a superposition of the optical image and the data set is performed on a monitor, and the optical image is taken with a video camera which is permanently connected to a 3D sensor for determining the three-dimensional position.

17. The method according to claim 14, wherein the step of generating a superposition of the optical image and the data set comprises interpolating a display of the data set between an eye of an observer and the jaw to be represented.

18. The method according to claim 17, wherein the interpolating step comprises displaying with a transparent LCD display.

19. The method according to claim 17, which comprises reflecting the data set into the observer's eye.

20. The method according to claim 14, which further comprises inserting three-dimensional structures into the data set of the image, and representing the image in the positionally correct relationship with the optical image.

21. The method according to claim 14, which further comprises removing the device following the taking step, and reinserting the device for positional determination into the oral cavity in a same position as in the taking step.

22. The method according to claim 14, wherein the generating step comprises generating a superposition of an optical image of the model of the jaw and the data set in a positionally correct relationship.

23. A method for representing a person's jaw and/or of a model thereof, which comprises:
   the preparatory steps of:
      inserting a device for positional determination into a person's oral cavity, the device having optically visible marking points;
      taking at least one picture of the person's jaw, including the marking points in the picture, and storing the picture in memory as a data set;
   and the representing steps of:
      bringing a 3D sensor to the jaw;
      preparing at least one photographic image of the jaw;
      removing the device for positional determination;
      preparing at least one further photographic image of the jaw from the same position;
      storing the photographic images in memory as a data set;
      finding a match of the marking points on the picture and the photographic image;
      superimposing an optical image of the jaw and the data set in a positionally correct relationship.

24. The method according to claim 23, wherein the taking step comprises taking an image with an imaging process selected from the group consisting of X-ray, CT, and MRI.

25. The method according to claim 23, which further comprises taking an impression of the jaw and forming a model of the jaw, and the bringing step comprises bringing the 3D sensor to the model of the jaw.

26. The method according to claim 23, which further comprises removing the device from the person's jaw after the taking step, and reinserting the device for positional determination into the oral cavity or into the model in a same position as in the taking step.

27. In combination with a system for representing one of a person's jaw and a model thereof, wherein a device for positional determination is inserted into a person's oral cavity, an image is taken of the person's jaw, the image is stored in memory as a data set; a 3D sensor is placed externally of the person's jaw or of the model thereof; a positional relationship between the 3D sensor and the device for positional determination is determined; and an optical image of the jaw or of the model is superimposed on the data set in the positionally correct relationship; a device for positional determination, comprising:

a device body adapted to be inserted into a person's oral cavity and to be held by the person's upper jaw and lower jaw in an unambiguously reproducible position, marking points defined on said device body which are identifiable by an imaging method, and a position sensor mounted on said device body for enabling precise determination of the three-dimensional position of the device.

28. The device of claim 27, wherein said device body is formed with a solid base body having said marking points and carrying said position sensor, and retention bodies of flexible, hardenable material formed on said solid base body, said retention bodies being adapted to conform to a shape in a person's oral cavity.

* * * * *